(12) United States Patent
Rheinnecker et al.

(10) Patent No.: US 8,287,913 B2
(45) Date of Patent: *Oct. 16, 2012

(54) METHOD AND APPARATUS FOR EXTRACTION OF PROTEIN MATERIAL FROM ARTHROPOD GLANDS AND A MEMBRANE FORMED THEREFROM

(75) Inventors: Michael Rheinnecker, Aachen (DE); Stefan Kohlhaas, Voerde (DE); Rolf Zimmat, Dusseldorf (DE)

(73) Assignee: Spin'Tec Engineering GmbH, Aachen (DE)

( * ) Notice: Subject to any disclaimer, the term of this patent is extended or adjusted under 35 U.S.C. 154(b) by 718 days.

This patent is subject to a terminal disclaimer.

(21) Appl. No.: 12/128,425

(22) Filed: May 28, 2008

(65) Prior Publication Data

US 2008/0293918 A1 Nov. 27, 2008

Related U.S. Application Data

(63) Continuation-in-part of application No. PCT/EP2007/001775, filed on Mar. 1, 2007.

(60) Provisional application No. 60/777,788, filed on Mar. 1, 2006.

(30) Foreign Application Priority Data

Mar. 1, 2006 (GB) .................................. 0604089.3

(51) Int. Cl.
*A61K 35/64* (2006.01)
(52) U.S. Cl. ..................................... 424/538; 435/283.1
(58) Field of Classification Search ........................ None
See application file for complete search history.

(56) References Cited

U.S. PATENT DOCUMENTS

| 6,858,168 | B1 * | 2/2005 | Vollrath et al. | 264/41 |
| 7,041,797 | B2 * | 5/2006 | Vollrath | 530/353 |
| 2005/0065323 | A1 * | 3/2005 | Vollrath | 530/353 |
| 2005/0281859 | A1 | 12/2005 | Knight et al. | |

(Continued)

FOREIGN PATENT DOCUMENTS

EP 1241178 A1 9/2002

(Continued)

OTHER PUBLICATIONS

Magoshi, Jun, et al., "Chapter 25: Mechanism of fiber formation of silkworm", "Silk Polymers", 1994, pp. 292-309, Publisher: American Chemical Society, Published in: Washington, D.C.

(Continued)

*Primary Examiner* — Christopher R. Tate
(74) *Attorney, Agent, or Firm* — Hultquist, PLLC; Steven J. Hultquist; Kelly K. Reynolds

(57) ABSTRACT

An apparatus and method for the extraction of material from glands of arthropods. The apparatus comprises a container in which at least part of the glands are placed and a buffer solution at least partially immersing the glands. Gland material is collected in the material collection area of container. In use the material is released from glands into the buffer solution and sedimented at the bottom of the container. The method comprises: a first step of removing from a body of the arthropod the gland containing at least partially the material; a second step of making an opening in an epithelium of the gland; and a third step of placing the gland in a container at least partially immersed in a buffer solution such that the materials exit the glands and sediments in the material collection area of the container.

8 Claims, 6 Drawing Sheets

U.S. PATENT DOCUMENTS

| | | |
|---|---|---|
| 2006/0188992 A1 | 8/2006 | Hagio et al. |
| 2006/0257854 A1 | 11/2006 | McDevitt et al. |
| 2008/0262384 A1 | 10/2008 | Wiederkehr et al. |
| 2009/0042215 A1 | 2/2009 | Ingham et al. |
| 2010/0152181 A1 | 6/2010 | Burkholder et al. |
| 2011/0081417 A1 | 4/2011 | Sargeant et al. |

FOREIGN PATENT DOCUMENTS

| | | | |
|---|---|---|---|
| EP | 1244828 B1 | | 4/2004 |
| GB | 385160 | | 12/1932 |
| JP | 51-67785 A | | 6/1976 |
| JP | 02-268693 A | | 11/1990 |
| JP | 03209399 | * | 9/1991 |
| JP | 09019238 | * | 1/1997 |
| JP | 09070241 | * | 3/1997 |
| JP | 2003-165843 A | | 6/2003 |
| JP | 2003-180335 A | | 7/2003 |
| JP | 2003180335 A | | 7/2003 |
| WO | 0234885 A1 | | 5/2002 |
| WO | 03037925 A2 | | 5/2003 |
| WO | 2005108983 A1 | | 11/2005 |
| WO | 2005123114 A2 | | 12/2005 |

OTHER PUBLICATIONS

"Sigma Aldrich Product Catalogue", 2006-2007, pp. E70, E71, and E87.

Altman, Gregory H., et al., "Silk-based biomaterials", "Biomaterials", Feb. 2003, pp. 401-416, vol. 24, No. 3.

Creighton, T.E., "Proteins: structures and molecular properties", 1993, Publisher: W. H. Freeman, 2nd Edition.

Freddi, G., et al., "Swelling and dissolution of silk fibroin (*Bombyx mori*) in N-methyl morpholine N-oxide", 1999, pp. 251-263, vol. 24.

Huemmerich, D., et al., "Processing and modification of films made from recombinant spider silk proteins", "Applied Physics A", 2006, pp. 219-222, vol. 82.

Inoue, S., et al., "Assembly of the silk fibroin elementary unit in endoplasmic reticulum and a role of L-chain for protection of . . . ", "Eur. J. Biochem.", 2004, pp. 356-366, vol. 271.

Jin, H., et al., "Mechanism of silk processing in insects and spiders", "Nature", 2003, pp. 1057-1061, vol. 424.

Li, M., et al., "Enzymatic degradation behavior of porous silk fibroin sheets", "Biomaterials", 2003, pp. 357-365, vol. 24.

Nazarov, R., et al., "Porous 3-D Scaffolds from Regenerated Silk Fibroin ", "Biomacromolecules", 2004, pp. 718-726, vol. 5.

Vallejo, L.F., et al, "Strategies for the recovery of active proteins through refolding of bacterial inclusion body proteins", "BioMed Central", 2004.

Co-pending Unpublished U.S. Appl. No. 12/486,977, filed May 18, 2009.

\* cited by examiner

Step 200:
> filling of container 10 with buffer 30 and optionally additives 40

Step 210:
> extraction of a gland 70 from body of arthropod
> introduction of one opening in epithelial cell wall of gland 70
> placement of opened gland 70 on gland elution device 50 with gland pick-up and transfer device 80

Step 220:
> release of gland content 90 into container 10 and collection on material collection area 20
> Optionally: homogenisation and adjustment of material properties of gland content 90 through variation of position of gland elution device 50 and support 60 relative to each other and to the position of material collection area 20.

Step 230
> storage of gland content inside container 10 or
> transfer to storage device

Fig. 3

METHOD AND APPARATUS FOR
EXTRACTION OF PROTEIN MATERIAL
FROM ARTHROPOD GLANDS AND A
MEMBRANE FORMED THEREFROM

CROSS-REFERENCE TO RELATED APPLICATIONS

This application is a continuation-in-part, filed under 35 USC 120, of International Patent Application No. PCT/EP2007/001775 filed Mar. 1, 2007 which in turn claims the benefit of priority of U.S. Provisional Patent Application No. 60/777,788 filed Mar. 1, 2006 and UK Patent Application No. 0604089.3 filed Mar. 1, 2006.

FIELD OF THE INVENTION

The present invention relates to an apparatus and method for the extraction of material from wild-type or recombinant arthropod glands.

DESCRIPTION OF THE RELATED PRIOR ART

Inoue et al in Eur. J. Biochem. 2004, 271, 356-366, described the secretion of native silk fibroin of *Bombyx mori* from the posterior silk gland as a 2.3 MDa elementary unit (hereinafter termed EU) which consists of six sets of a disulfide-linked heavy chain-light chain fibroin heterodimer and one molecule of P25.

Currently, solutions of silk proteins (such as fibroin and other proteins) are made as regenerated silk solutions out of cocoons or silk threads which are dissolved in solubilisation agents (e.g. lithium bromide) and refolded through dialysis or other buffer exchange techniques (see, for example, Altmann et al., Biomaterials 2003, 24, 401-416). Given the known challenges in producing active proteins through refolding after solubilisation in protein folding/chaotropic agents (Vallejo and Rinas, Microbial Cell Factories, 2004, doi: 10.1186/1475-2859-3-11), a person skilled in the art will appreciate the technical hurdles which have to be solved in order to produce correctly folded, native fibroin EUs from regenerated silk solutions. It is therefore not surprising that there has been no report to date on the successful production of high molecular weight fibroin assembled in EU conformation out of regenerated silk solutions.

The differences between the native silk proteins as produced and stored in the glands of arthropods, such as silkworms, (i.e. in their high molecular weigh EU conformation) and the regenerated silk proteins (disclosed above) are such that the regenerated silk proteins produced by current techniques have at most "native-like" features, i.e. the regenerated silk proteins have some properties in common but cannot be said to be identical or substantially identical with the native silk proteins. The native silk proteins are defined as those proteins found in their native protein conformation, i.e. with the primary, secondary, tertiary and quaternary folding structures similar or essentially similar to the wild type protein (Thomas E. Creighton, Proteins, Second Edition, 1993, 232-236, ISBN 0-7167-2317-4). The differences of regenerated silk proteins in their protein folding pattern, especially for their tertiary and quaternary folding compared to native silk proteins have apparently no negative impact on their use as cosmetic or pharmaceutical ingredients (as described, for example, by Tsubouchi et al. in international patent application PCT/JP01/02250). However, for more demanding applications, such as the production of mechanically strong films, coatings and moulded objects or the biomimetic spinning of silks (as described by Vollrath and Knight in European Patent 1244828, assigned to Spintec Engineering GmbH), the correct folding and self-assembly of the silk proteins used for production of said materials plays a role in determining the mechanical strength and functional features of the formed materials.

Due to the differences between the regenerated silk proteins and the native silk proteins noted above, the quality of regenerated silks has not been sufficient for the production of high quality silk materials through moulding, coating or biomimetic spinning as described in the above mentioned European patent 1244828. For example, Huemmerich et al. reported in Appl. Phys. A 2006, 82, 219-222 that cast silk membranes made out of regenerated artificial silk peptides had to be treated with potassium phosphate or methanol in order to improve the physical strength of the membranes and convert them from water soluble to water resistant membranes.

Another example is provided in international patent application number WO 2004/000915 which describes regenerated silk membranes which require cross-linking with alcohols to improve the inferior mechanical properties of the cast silk films.

In international patent application number WO 2005/012606, the chemicals PEG or PEO are used in an effort improve the known brittleness of regenerated silk protein membranes. A further example for using physico-chemical treatments to improve regenerated silk protein membranes is the use of a cross-linking agent followed by a freeze-drying method as described by Li et al. in Biomaterials 2003, 24: 357-365.

European Patent Application No 1241178 (assigned to the National Institute of Agrobiological Sciences and Kowa Co) teaches a method for the production of silk fibroin by dissolving cocoons in an aqueous alkaline solution or an aqueous urea solution. The aqueous alkaline solution described in the examples of the '178 patent application is sodium carbonate or lithium thiocyanate at a pH of 7. Subsequently acetone or alcohol is added to the aqueous alkaline solution to precipitate the fibroin. The results shown in the patent application do not indicate that high molecular weight silk proteins exhibiting native tertiary and quaternary protein folding conformations were produced. The '178 patent application reports (paragraph 18) also a method in which the silk gland is extracted from the body of a silkworm followed by extraction of the protein from a silk gland lumen. The disclosure suggests, however, that the process is not suitable for industrial production because the fibroin obtained contains impurities such as silkworm humor and silkworm gland cells.

A method for the extraction of native silk proteins from silkworm glands has been described in U.S. Pat. No. 7,041, 797 (Vollrath, assigned to Spintec Engineering GmbH). The '797 patent describes an approach in which the silk glands are removed from the body of the silkworm followed by removal of an epithelial layer of the silk glands. The method works well for the manual extraction from individual ones of the silk glands. However, it is tedious and time consuming if a larger number of the silk glands need to be extracted. It is thus impracticable as a production method for the native proteins from the silk glands on a large industrial scale. The inventor of the '797 patent has also not detailed a method or an apparatus which allows for the efficient and homogeneous mixing and pooling of proteins extracted from the silk glands as well as for the incorporation of additives in the extracted content from the silk gland.

Similarly Japanese Patent Application JP-A-2268693 (Asahi) teaches a method of cultivating a silk gland obtained from silkworms (such as from *Bombyx mori*) and using a culture medium. The culture medium is removed using dialysis to obtain an aqueous solution of the silk fibroin. However, the inventors in the '693 patent application did not consider how to incorporate additives homogenously into the highly viscous content of the silk gland.

A cruder method for obtaining fibroin protein is disclosed in Japanese Patent Application J P-A-3209399 (Terumo) in which the heads are cut off of grown silkworms. The fibroin protein is then harvested by pressing the abdomen of the silkworm to extract the fibroin protein. Sericin is removed from the resulting protein mixture by treating the protein mixture with a weak alkali, such as $Na_2CO_3$. The inventors of the '399 patent application did not teach how to include additives in the protein mixtures. Further the method of the '399 patent application has the disadvantage that incorporation of impurities from the silkworm body is not easily avoided. These impurities have to be removed or they may affect the properties of biomimetically spun fibres or of coated or moulded objects produced with said protein mixtures.

A disadvantage when using non-native, regenerated silk fibroin as feedstock for casting silk membranes is due to the presence of a distinct granular or globular morphology (a so-called "ultrastructure") when analysed by SEM (scanning electron microscopy). As reported by Jin and Kaplan in Nature, 2003, Vol 424, 1057-1061). This SEM ultrastructure is caused by the aggregation of individual silk fibroin micelles during the drying process of the cast silk fibroin solution. According to Jin and Kaplan, those micelles can also give rise to larger globular structures with diameters of up to 15 µm (see also Nazarov et al. Biomacromolecules 2004, 5, 718-726). Micellar-like morphology has also been demonstrated at high resolution SEM (2 µm scale) by Jin and Kaplan to occur in methanol treated, natural silk protein isolated from the silk glands of *Bombyx mori* silkworms (Nature, 2003). The fibroin micelles have also been reported by G. Freddi et al. in Int J Biomacromolecules 1999, 24: 251-263 as densely packed, roundish particles with diameters of around 200 nm. Because of the granular ultrastructure of regenerated silk membranes, it has not been possible yet to manufacture mechanically strong, regenerated silk membranes with pore sizes below 0.2 µm which are required in medical applications as effective physical barrier against antimicrobial and antiviral contamination. In addition, the aggregated fibroin micelles in regenerated silk membrane hinder development of advanced optical and electronics applications which require non-granular ultrastructural morphologies.

SUMMARY OF THE INVENTION

There is therefore a need for a method and apparatus to efficiently extract native proteins from arthropod glands.

There is furthermore a need to incorporate additives into said arthropod gland proteins.

There is furthermore a need to homogenously mix arthropod gland proteins extracted from more than one arthropod.

There is furthermore a need to obtain a strong silk protein membrane which has pore sizes smaller than 200 nm for the protection against microbial and viral contamination.

These and other objects are solved by an apparatus for the extraction of material from a gland of an arthropod (such as a silkworm) comprising a holding device by which at least part of the gland is held. A buffer solution at least partially (but not necessarily completely) immerses the gland. The material is released from the gland into the buffer solution.

The material is ultimately sedimented in a collection area at the bottom of the apparatus.

The apparatus ensures that material from the two or more silkworm glands from one or more arthropods (such as silkworms) is substantially homogenously mixed together in the apparatus. At least partially immersing the silkworm gland in the buffer solution means that osmotic pressure, enzymatic or mechanical dissection ensures that the material is released from the silkworm gland into the buffer solution.

The apparatus further incorporates a porous support, such as a porous net or a porous plate, which is placed between the holding device and the collection area of the material. The porous support provides an efficient technical solution for breaking up the highly viscous protein content flowing out of the glands, resulting in a uniformly mixed material collected in the collection area.

The porous support also serves as a filter medium to prevent unwanted contaminants entering the collection area of the material.

The porous support also serves as a technical means to control and change material properties of the collected material (i.e. the contents of the gland). For example, by changing the mesh or pore size and/or adjusting the position of the porous support relative to the position of the gland on the holding device and/or relative to the position of the collection area of the apparatus, it is possible to control exposure of the material to the buffer solution (and any additives in the buffer solution) in the apparatus. In a further embodiment, the exposure of the material to the buffer solution can also be controlled by using a non-porous support whereby the position of the non-porous support is such that the material is guided towards the collection area of the apparatus.

Additives can be incorporated into the buffer solution. It has been found that the solubilisation and sedimentation of the material in the buffer solution leads to a substantially even distribution of additives within the material.

These and other objects are also solved by a method comprising: Providing a gland containing at least partially the material; making an opening in the gland and positioning the gland by a holding device such that the gland is at least partially immersed in a buffer solution such that the material can exit the gland.

It is also possible to pass the material through a porous support (such as a porous plate or a porous net). As discussed above the provision of the porous support breaks up the highly viscous protein content flowing out of the glands which results in a uniformly mixed material collected in the collection area. Finally the material is collected at the bottom of the apparatus.

As is discussed below, the material consists of native or recombinant biomaterials which can be produced in arthropod glands such as for example proteins, peptides or carbohydrates or other suitable biological molecules and/or a combination of these. The materials can be used for a number of purposes including, but not limited to, the manufacture of fibres or films. Preferably the material is native or recombinant fibroin or fibroinfusion proteins known to one skilled in the art of recombinant silkworm technologies.

Extraction of arthropod protein in accordance with the invention avoids the need to use protein refolding techniques as is necessary if silk proteins are made from regenerated silk solution. Instead, the apparatus and method presented here enables a large scale extraction of native materials made and stored by the arthropod in the glands. By avoiding the protein refolding techniques and by using mild protein purification conditions, all or most of the functionality conferred by natural synthesis of the biomaterial in the arthropod's glands can be retained. For example, in the case of the silkworm the disclosed invention allows an efficient harvesting of native fibroin or recombinant fibroin without destroying high molecular weight multimeric fibroin protein complexes (tertiary and quaternary folding, described for example in Inoue et al in Eur. J. Biochem. 2004, 271, 356-366) by avoiding the use of denaturing agents which are widely used for making regenerated silks (for example see Altmann et al., Biomaterials 2003, 24, 401-416). From a commercial point of view, the disclosed apparatus enables a benign harvesting technique and preservation of the native features of fibroin in the extracted silkworm gland content. In addition, the apparatus forms the basis for the production of novel films, coatings, moulded objects or spun silk materials based on the enhanced properties of native compared with regenerated silk proteins.

Furthermore, the invention enables the mixing of the arthropod gland content with buffer and/or additives, thereby providing a means for the production of novel silks with properties conferred by the permanent or transient integration of additives. Since the solution is an aqueous solution and does not require any organic solvents as refolding agents for silk proteins (unlike the prior art discussed above), it is believed that, for example, any labile protein or peptide can be used as additives. Other examples of potential additives are listed below.

The invention also enables the homogenisation of the extracted gland content by passage through a porous net, thereby providing for homogenous mixing of the gland contents from more than one arthropod.

In summary, the disclosed apparatus enables the operator to manufacture gland content solutions with tuneable material properties such as for example protein concentration or biochemical composition by controlling parameters such as buffer composition, dimensions of openings in a porous support, flow distance of materials inside the apparatus and size of the collection area.

DESCRIPTION OF THE DRAWINGS

FIG. 3 shows the method of use of the apparatus.

DETAILED DESCRIPTION OF THE INVENTION

For a complete understanding of the present invention and the advantages thereof, reference is now made to the following detailed description taken in conjunction with the Figures.

It should be appreciated that the various aspects of the invention discussed herein are merely illustrative of the specific ways to make and use the invention and do not therefore limit the scope of invention when taken into consideration with the claims and the following detailed description. In particular it should be noted that features of one embodiment of the invention may be combined with features of other embodiments of the invention.

Figure 1:
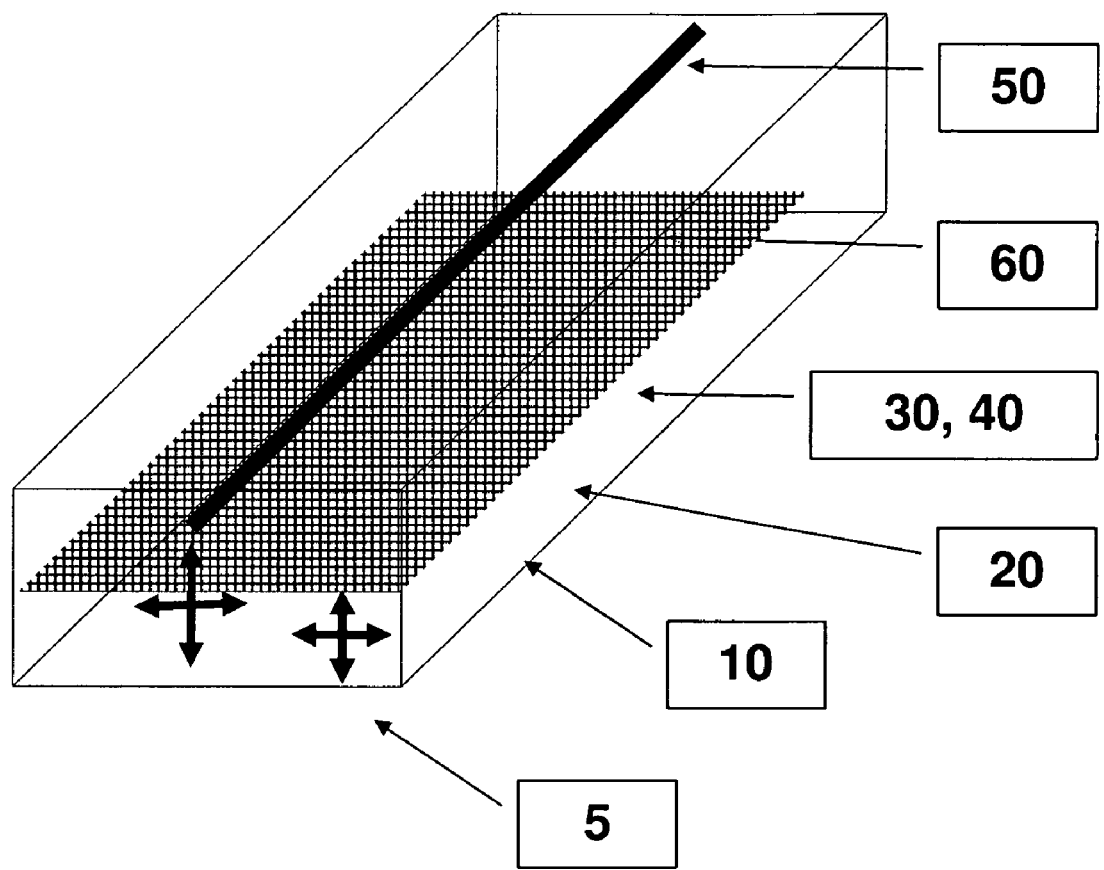
FIG. 1 shows the apparatus with a porous support.
Figure 2:
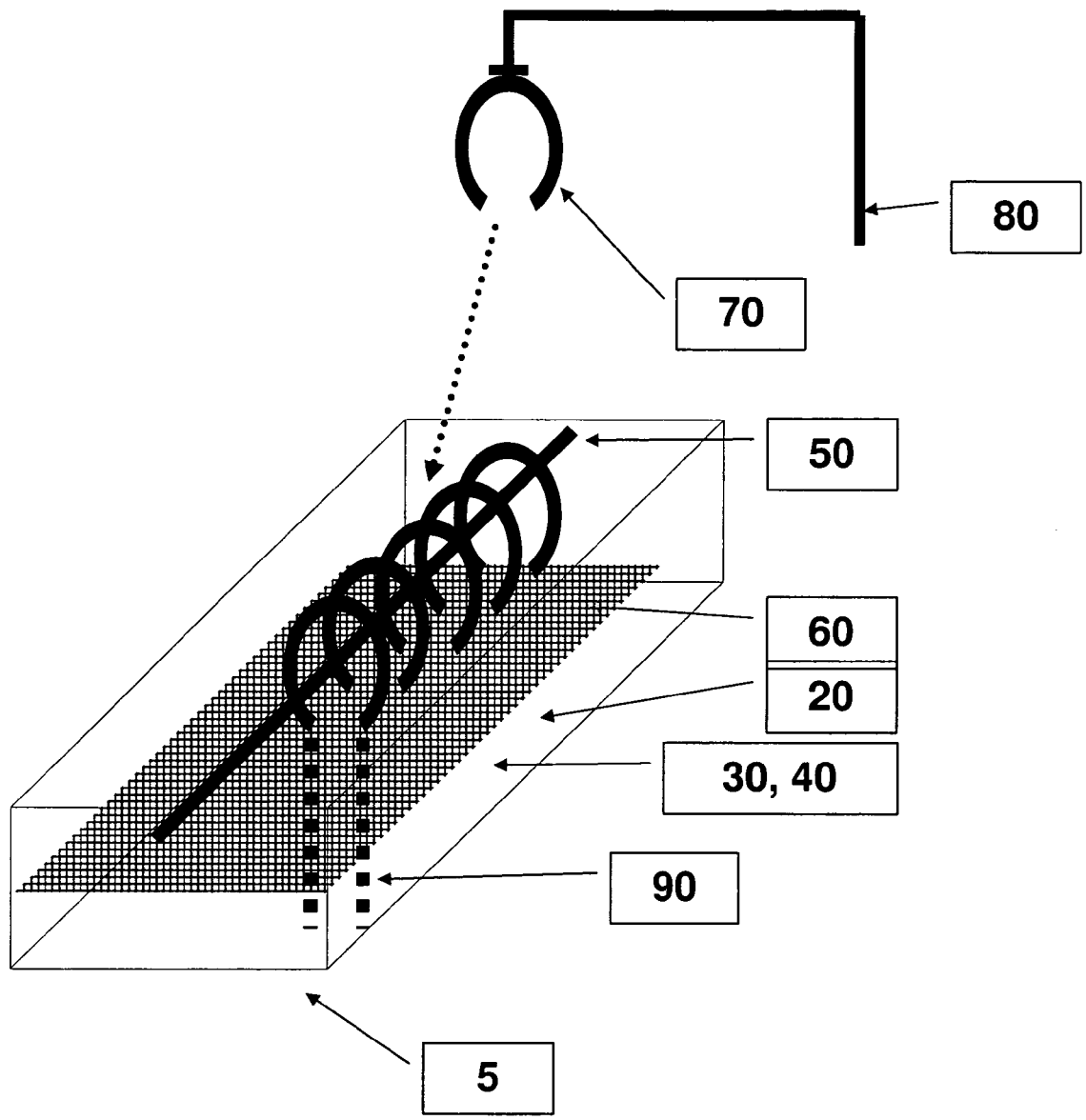
FIG. 2 shows the use of the apparatus for harvesting arthropod gland contents.
Figure 5:
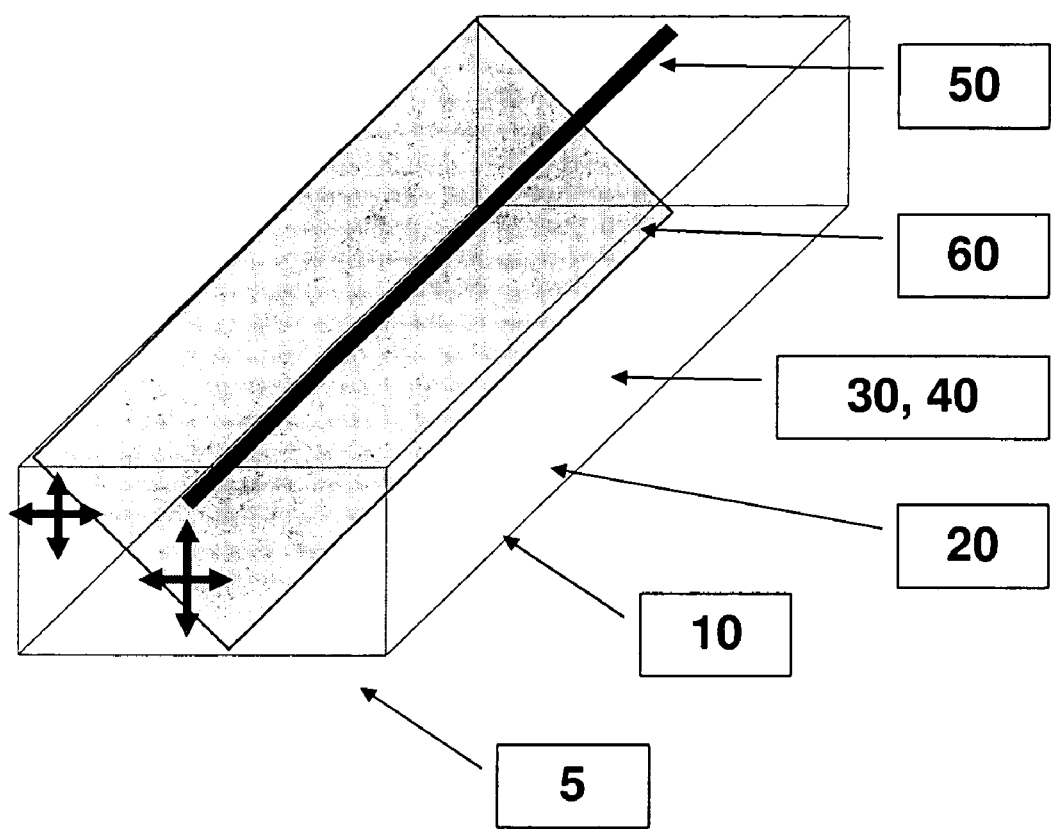
FIG. 5 shows the apparatus with a solid support.

The teachings of the cited documents should incorporated by reference into the description FIGS. 1, 2 and 5 show an apparatus 5 according to the present invention. The apparatus 5 comprises a container 10, a material collection area 20, and a buffer solution 30 with one or more additives 40. The one or more additives 40 may be added at any stage during the use of the apparatus or alternatively no additives 40 need to be added. The apparatus 5 further contains a height adjustable (indicated by the arrow) gland holding device 50 which holds one or more arthropod glands removed from arthropods in position to facilitate release (elution) of the contents of the one or more glands. Optionally, the apparatus 5 contains a height and position adjustable (indicated by the arrows) support 60 with a pore size of 0.1-10 mm. The support 60 can be a porous net or a porous plate as indicated in FIG. 1 or a solid plate as indicated by FIG. 5. The buffer solution 30 may contain for example 100 mM Tris or any other buffer type known to one skilled in the art of protein purification. The additives 40 may be by way of example only a therapeutically active substances or colouring agents.

The method of use of the apparatus 5 for extracting arthropod gland content is shown in overview in FIG. 2 and is described in FIG. 3.

FIG. 2 shows the placement of the arthropod glands 70 on the holding device 50 (indicated by the arrow). To facilitate industrial harvesting of the silkworm glands. The holding device 50 is automatically loaded with the arthropod glands 70 by one or several robotic gland pick-up and transfer devices 80. However, for small scale production, the apparatus 5 can also be loaded manually. The gland content material 90 is released out of the arthropod gland 70 and is collected in the material collection area 20. Optionally, the porous support 60 may be used to improve homogeneous mixing with and increase exposure of the gland content 90 to the buffer 30 with or without the additives 40. By changing the positions of holding device 50 and porous support 60 relative to each other and relative to the material collection area 20, the apparatus 5 enables adjustment of the required concentration of the collected gland content 90. Alternatively, no porous support 60 may be used at all thereby preserving the concentration of eluted gland content 90 as much as possible.

FIG. 3 summarises the method of use for apparatus 10.

In a first step 200 the container 10 is filled with the buffer 30.

In a further aspect of the present invention the container 10 may or may not be filled with one or more additives 40.

In a next step 210, the glands 70 are extracted from bodies of the arthropods, such as silkworms. This can be done, for example, using a method described in U.S. Pat. No. 7,041, 797. At least one opening is made into an epithelial cell wall of the silkworm glands so that the content (silk proteins) can be released from the inside of the silkworm glands. The opening in the epithelial cell wall can be made by ultrasound, mechanical cutting or enzymatic dissection. The opening in the epithelial cell wall can also be carried out by cutting the silkworm gland roughly in half. The exact position of the opening in the epithelial cell wall and method of making the opening are not crucial for practicing the invention. The opened glands 70 are then placed either manually or with one of the robotic pick-up and transfer devices 80 onto the holding device 50 of the apparatus 10. Such pick-and-place devices are known to one skilled in the art of laboratory automation and allow the physical manipulation of the silkworm gland 70 by means of a pick-and-place functional device, such as a gripper. The transferred silkworm glands 70 are arranged on the holding device 50 in a manner enabling the efficient release of the content 90 of the silkworm gland 70 and an efficient packing of the silkworm glands 70 inside the container 10. In one embodiment of the invention, the silkworm glands 70 from about 7 silkworms are used, however this is not limiting of the invention and can be easily scaled up to several magnitudes by increasing the dimensions of the holding device 50 and of the apparatus 5.

In the next step 220, gland content 90 flows out of the silkworm gland 70 into the container 10 and is collected in the material collection area 20. The silkworm gland 70 is at least partially immersed. Optionally, the gland content 90 passes through porous support 60. As discussed above, the use of the porous support 60 has the advantage of improving homogeneity and adjusting material properties of the gland content 90 by varying the positions of the porous support 60 and/or the holding device 50 in the container 10. In addition, the porous support 60 may also be used for reducing impurities from the released gland content 90.

In step 230, the gland content 90 collected in the material collection area 20 may be stored in the container 10 or transferred into a further suitable storage container (not shown). The collected gland content 90 has a protein content of around 1-30% and can be loaded with useful additives during or after the extraction process to confer novel functionality to the collected gland material. In addition, the collected gland content 90 is substantially homogeneous, especially if the collected gland content 90 was passed through the porous support 60. This homogeneous distribution of the collected gland content 90 and the ability to confer the one or more additives to the gland contents 90 contrasts with prior art methods in which it has not been possible to mix the material native silk proteins from more than one silkworm gland 70 or to incorporate the one or more additives 40 into the material.

It should be noted that this method is equally applicable to native proteins and peptides (not only limited to silk proteins) and their recombinant analogous and fusion proteins extracted in native form from the glands of wild type or recombinant arthropods such as silkworms from the family Bombycidae, including but not limited to silkworms from the genera *Antherea, Attacus, Samia, Bombyx* and *Telea*. The extracted materials include, but are not limited to, ABAB-block polymer type peptides and proteins, such as fibroin.

The one or more additives 40 can be added to the extracted gland content 90, either to the buffer solution 30 at any stage of the extraction or directly to gland content 90 harvested in the material collection area 20.

The range of additives 40 that can be added is extensive and it is envisaged that the following additives 40 could be used:
  Organic Additives
  Small molecular entities
  Peptides
  Proteins
  Carbohydrates
  Lipids
  Nucleic acids such as DNA, RNA, PNAs and other nucleic acid analogues with more than 100 bases length as well as fragments thereof with less than 100 bases length such as for example siRNAs
  Inorganic Additives:
  Additives or precursors that improve or render mechanical, optical, electrical or catalytic properties
  Minerals such as phosphates, carbonates, sulphates, fluorides, silicates etc. and mineraloids such as clays, talc, and silicas,
  Salts of alkali and alkaline earth metals, transition metals, post transition metals and alloys thereof,
  Metal complexes such as metal ions coordinated with EDTA or other chelating agents,
  Insulators such as metal oxides like Fe2O3, Al2O3, TiO2,
  Any III-V or II-VI semiconductor and conductors, such as metals and alloys thereof,
  Carbon-based additives, such as fullerenes, carbon nanotubes, fibres or rods, graphite
  Hydrophobic, hydrophilic or amphiphilic additives to adjust the solubility of the gland content in the buffer solution and thus provide differing concentrations of extracted material.
  Nanoparticles
  Physiologically active compounds such as
  Antibodies and their analogous
  Antiseptics, antiviral agents and antibiotics
  Anti-coagulants and anti-thrombotics
  Vasodilatory agents
  Chemotherapeutic agents
  Anti-proliferative agents
  Anti-rejection or immunosuppressive agents
  Agents acting on the central and peripheral nervous system
  Analgesics
  Anti-inflammatory agents
  Hormones such as steroids
  Mineralization agents for tooth regeneration such as fluorapatite for tooth regeneration
  Mineralization agents for bone regeneration such as hydroxylapatite, tricalcium phosphate, marine animal derived particles such as corals and chitosans and the like
   Growth factors such as
   bone morphogenic proteins BMPs
   bone morphogenic-like proteins GFD's
   epidermal growth factors EGFs
   fibroblast growth factors FGFs
   transforming growth factors TGFs
   vascular endothelial growth factors VEGFs
   insulin-like growth factors IGFs
   nerve repair and regeneration factors NGFs
   platelet-derived growth factors PDGFs
  Proteins functioning as cell or protein binding agents such as collagen IV, polylysine, fibronectin, cadherins, ICAM, V-CAM, N-CAM, selectins, neurofascins, oxonin, neuroglinin, fascilin
  Cell-binding motives such as for example the RGD or RADAR recognition sites for cell adhesion molecules
   Wound healing agents
   Agents for preventing scar-formation such as for example Cordaneurin
  Other naturally derived or genetically engineered therapeutically active proteins, polysaccharides, glycoproteins or lipoproteins
  Therapeutically active cells such as for example stem cells or autologous cells derived from a site of the patient
  Agents for detecting changes of pH such as neutral red
  Agents promoting 1-sheet formation of the extracted gland proteins
  Agents such as biodegradable polymers which degrade at controllable rates thereby enabling controlled biodegradability
  Agents such as protease inhibitors which inhibit protease activity for example in the site of implantation in the patient thereby enabling controlled biodegradability
  Aprotic solvents improving hydrogen bond formation in silk proteins such as ether, ester, acidanhydride, ketones (e.g. acetone), tertiary amines, dimethylformamide, pyridine, furane, thiophen, trichlorethane, chloroform and other halogenated hydrocarbons, dimethylsulphoxide, dimethylsulphate, dimethylcarbonate, imsol, anisol, nitromethane.
  Agents enhancing release of physiologically active compounds
   Naturally derived or chemically synthesised dyes Naturally derived or genetically engineered colouring agents such as green fluorescent protein Naturally derived or genetically engineered structural load bearing proteins such as actin, silk, collagen or fibronectin and analogous or derivates thereof.

Electrically conducting and semi-conducting materials

Polyelectrolytes with bound positive or negative charges

Ionic liquids

Materials conferring transient or permanent magnetism

Water soluble polymers such as polylactic acid or polycaprolactone

Glass fibres

It should be understood that the list of additives is not intended to be limiting of the invention but is exemplary of the additives that can be added to the extracted gland material 90.

The extracted gland material 90 can be used for forming objects, for example by coating, moulding or spinning as defined in the spinning apparatus disclosed in European Patent 1244828. If the one or more additives 40 are added to the extracted gland material 90, the formed objects can have additional properties. For example, one of the additives 40 to encourage the growth of tissue could be added to the extracted gland material 90 so that the formed objects can be used as a medical implant.

EXAMPLES

Example 1

The silkworm glands 70 of four *Bombyx mori* silkworms at the end of their fifth instar were extracted by removing the silkworm gland 70 from the body of the *Bombyx mori* silkworms as described above with reference to the U.S. Pat. No. 7,041,797. Each of the silkworm glands was cut into half. The posterior halves of the silkworm glands 70 were placed with a pair of forceps on a net positioned inside a Petri dish which was filled with 100 mM ammonium acetate buffer having a pH 7.8. In total, eight posterior silkworm glands 70 were transferred. The eight silkworm glands 70 were incubated for 60 min for osmotic shock and release of the content of the silkworm gland 70. The emptied silkworm glands 70 were then removed from the surface of the net using a pair of forceps. Where necessary, a sliding movement over the edge of the Petri dish was used in order to extract any remaining silkworm gland material left inside the silkworm gland. The extracted silkworm gland material was left overnight on the surface of the net which allowed the silkworm gland material to pass through the net and sediment at the bottom of the Petri dish. The net was then removed from the Petri dish and the silkworm protein from the silkworm gland harvested using a 5 ml disposable syringe.

Example 2

Eight posterior halves of the silkworm glands 70 were extracted as described in Example 1. Microscopic analysis of any remaining material stuck to the net and of the filtered gland content collected in the Petri dish demonstrated the efficient separation of epithelial cell debris and decomposed, denatured gland materials from the homogeneous gland content in the Petri dish.

Example 3

To demonstrate the possibility of incorporating additives 40 ("dopants") in the gland content during the extraction, eight posterior halves of the silkworm glands were extracted in a buffer solution 30 of 100 mM ammonium acetate buffer and an additive 40, of 1.75 mM neutral red. The buffer solution 30 had a pH 7.8. This was compared with four posterior halves extracted in 100 mM ammonium acetate buffer solution 30 at pH 7.8 without further additives 40. The addition of the additive 40 to the buffer solution did not lead to aggregation or destabilisation of the extracted gland material 90 from the silkworm gland.

The gland material containing the neutral red additive 40 was transferred into a Petri dish and dried at 50° C. to form a film. The film was found to be stable and retained red colour when incubated in water at room temperature for three months, thus demonstrating the stable integration of the additive into the gland material.

The silkworm gland material was extracted as described above containing 0.18 mM neutral red additive 40 was further tested successfully for spinnability using the biomimetic spinning device of European Patent 1244828 yielding uniformly red coloured silk fibres with diameter of about 5 μm collected on two aluminium reels.

Example 4

Material Properties of Extracted Gland Materials

Figure 4:
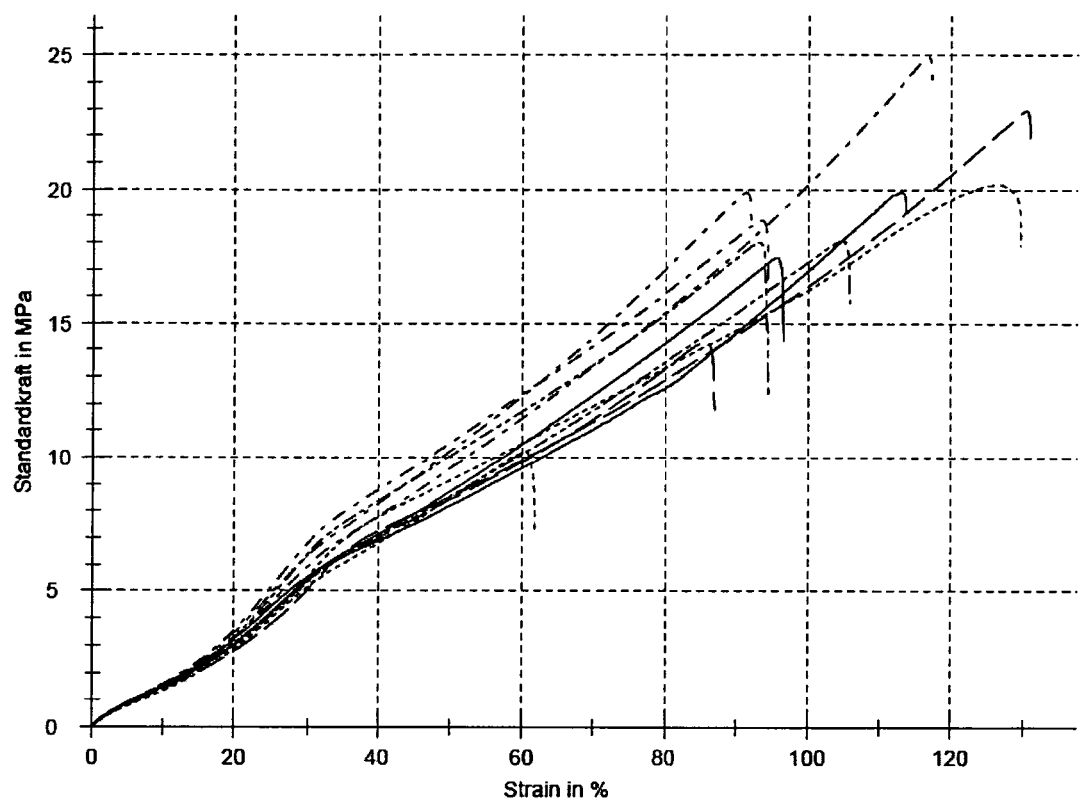
FIG. 4 shows the stress strain curve of Example 4.
Figure 6:
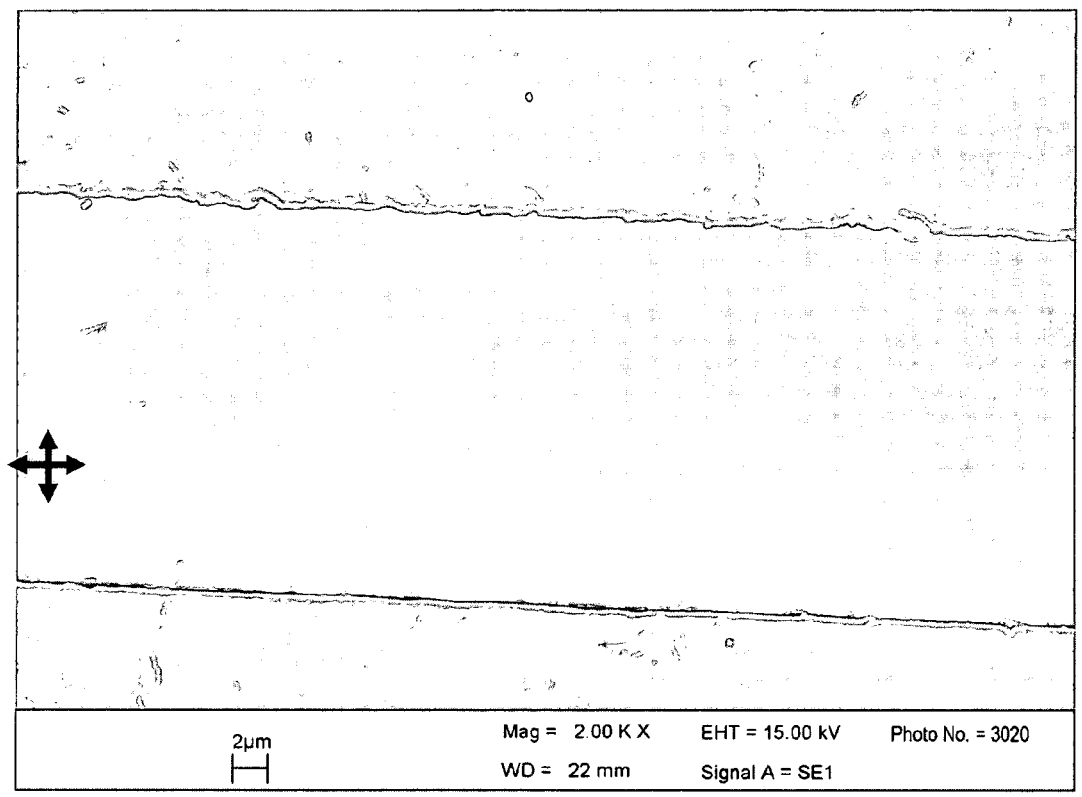
FIG. 6 shows a cross sectional SEM analysis of a silk membrane.

A film was cast using the gland material extracted in accordance with the method of Example 1. The cast film was water insoluble and did not change its properties upon repeated wetting and drying in water or organic solvents. Tensile testing was performed in d-$H_2O$ on a ZwickRoell TC-FR2.5TN tensile tester at 10 mm/min with sample geometries of 40 mm×2.5 mm×0.06 mm. The film exhibited breaking strength in d-$H_2O$ of about 20 MPa at approximately 100% breaking elongation (for data see FIG. 4). Cross-sections of the film were analysed by a Scanning Electron Microscope (SEM) at high resolution. FIG. 6 (scale bar 2 μm) demonstrates a homogenous SEM ultrastructure of the silk fibroin membrane without detectable pores and without a detectable granular or micellar-like morphology.

Example 5

Reproducibility of Gland Content Extraction

The silkworm glands of seven *Bombyx mori* silkworms at the end of their fifth instar were extracted by removing the silkworm gland from the body of the silkworms as described for example in the U.S. Pat. No. 7,041,797. Each of the silkworm glands was cut into half. The posterior halves of the silkworm glands (in total 14) were placed with a pair of forceps on a bar positioned at the top of a cylinder with approx. 30 mm diameter and approx. 100 mm length containing a 100 mM ammonium acetate, pH 7.8 buffer and a net with mesh size 1 mm, positioned at approx. 46 mm distance from the closed bottom of the cylinder. The whole content of the opened silk glands was released, passed through the net and collected at the bottom of the collection area 20. The protein concentration of the collected whole gland content was then determined by drying in an oven at 60° C. The extraction procedure was performed five times, yielding gland protein concentrations of 7.0%, 7.2%, 7.2%, 6.7% and 7.1% and an overall protein concentration of 7±0.22%

Example 6

Adjusting Protein Concentration of Extracted Gland Content

Four silk gland extractions with 14 posterior halves each were performed with the apparatus. For each one of the silk gland extractions, 14 posterior halves were prepared as described in Example 5. The concentration of the extracted gland content was adjusted by varying the position of the porous net to the bottom of the cylinder between 10 mm, 20 mm and 46 mm. One of the extractions was performed with the porous net removed allowing direct passage of the gland content from the gland to the bottom of the cylinder. The protein concentration of the collected whole gland content was then determined by drying in an oven at 60° C. The resulting protein concentrations were: 20% for extraction without the porous net, 15% with the porous net positioned at 10 mm distance from the bottom of the cylinder, 11% with 20 mm distance, 7% with 46 mm distance and 5% with 100 mm distance.

The invention claimed is:

1. A method for the extraction and mixing of material from glands of at least two wild type or recombinant arthropods comprising:
    providing the glands containing at least partially the material;
    making an opening in the glands;
    placing the open glands on a holding device, the open glands being at least partially immersed in a buffer solution such that the material is released from the open glands;
    collecting the released material on a porous support immersed in a buffer solution;
    passing the released material through the porous support so as to mix the material; and
    collecting the mixed material in a material collection area, wherein the material is selected from the group consisting of proteins, peptides and combinations thereof.

2. The method of claim 1, wherein the material is fibroin.

3. The method of claim 1, wherein the arthropod can be any native or recombinant species from the family Bombycidae.

4. The method of claim 1, further comprising adding at least one additive to the buffer solution.

5. The method of claim 4, wherein at least one additive is a biologically active molecule.

6. The method of claim 1, further comprising an adjustment of a distance between the gland holding device and/or a porous support and a material collection area.

7. The method of claim 1, further comprising an adjustment of a distance between the support and a material collection area.

8. The method of claim 1, wherein providing the gland comprises the removal of the gland from a body of the arthropod.

* * * * *